United States Patent
Miller

[11] Patent Number: 6,045,703
[45] Date of Patent: Apr. 4, 2000

[54] SEPARATION PROCESSES

[75] Inventor: Jay Fingeret Miller, Charleston, W. Va.

[73] Assignee: Union Carbide Chemicals & Plastics Technology Corporation, Danbury, Conn.

[21] Appl. No.: 09/094,651

[22] Filed: Jun. 15, 1998

[51] Int. Cl.[7] .................................................. B01D 15/08
[52] U.S. Cl. .......................................... 210/659; 540/540
[58] Field of Search ........................... 540/540; 210/656, 210/659, 635, 198.2, 774; 585/825

[56] References Cited

U.S. PATENT DOCUMENTS

| | | | |
|---|---|---|---|
| 2,985,589 | 5/1961 | Broughton et al. | 210/34 |
| 3,201,491 | 8/1965 | Stine et al. | 260/676 |
| 3,558,732 | 1/1971 | Neuzil et al. | 260/674 |
| 3,706,812 | 12/1972 | de Rosset et al. | 260/674 SA |
| 3,867,470 | 2/1975 | Van Grinsven et al. | 260/674 SA |
| 3,898,213 | 8/1975 | Koff | 540/540 |
| 3,899,485 | 8/1975 | Immel | 540/540 |
| 3,939,221 | 2/1976 | Pearce | 260/674 SA |
| 3,943,149 | 3/1976 | Hauck | 260/340.5 |
| 3,960,846 | 6/1976 | Potin | 540/540 |
| 3,966,712 | 6/1976 | Immel | 540/540 |
| 4,014,949 | 3/1977 | Hedge | 260/674 SA |
| 4,029,717 | 6/1977 | Healy et al. | 260/674 SA |
| 4,079,094 | 3/1978 | Rosback et al. | 260/674 SA |
| 4,140,686 | 2/1979 | Kawamoto | 540/540 |
| 4,182,633 | 1/1980 | Ishikawa et al. | 127/46 A |
| 4,267,054 | 5/1981 | Yoritomi et al. | 210/659 |
| 4,326,092 | 4/1982 | Neuzil | 585/828 |
| 4,345,946 | 8/1982 | Tu et al. | 127/46.3 |
| 4,372,857 | 2/1983 | Matthews et al. | 210/673 |
| 4,386,225 | 5/1983 | Neuzil | 568/758 |
| 4,402,832 | 9/1983 | Gerhold | 210/659 |
| 4,405,455 | 9/1983 | Ando et al. | 210/191 |
| 4,409,033 | 10/1983 | LeRoy et al. | 127/46.2 |
| 4,478,721 | 10/1984 | Gerhold | 210/659 |
| 4,486,618 | 12/1984 | Kulprathipanja et al. | 585/829 |
| 4,497,972 | 2/1985 | Neuzil et al. | 585/828 |
| 4,522,726 | 6/1985 | Berry et al. | 210/660 |
| 4,529,828 | 7/1985 | Antos et al. | 585/828 |
| 4,593,149 | 6/1986 | Barthomeuf | 585/828 |
| 4,655,796 | 4/1987 | Pirkle | 55/3 |
| 4,705,627 | 11/1987 | Miwa et al. | 210/264 |
| 4,734,199 | 3/1988 | Nagji et al. | 210/674 |
| 4,804,754 | 2/1989 | De Decker | 540/540 |
| 4,864,069 | 9/1989 | Zinnen | 585/828 |
| 4,876,390 | 10/1989 | McCulloch | 568/34 |
| 4,882,430 | 11/1989 | Neubauer | 540/540 |
| 4,886,929 | 12/1989 | Neuzil et al. | 585/828 |
| 4,886,930 | 12/1989 | Zinnen | 585/828 |
| 4,940,830 | 7/1990 | Zinnen et al. | 585/828 |
| 5,012,038 | 4/1991 | Zinnen | 585/828 |
| 5,017,735 | 5/1991 | Fellmann | 585/820 |
| 5,057,643 | 10/1991 | Zinnen | 585/828 |
| 5,064,539 | 11/1991 | Tanimura | 210/659 |
| 5,093,004 | 3/1992 | Hotier et al. | 210/659 |
| 5,102,553 | 4/1992 | Kearney et al. | 210/659 |
| 5,107,062 | 4/1992 | Zinnen | 585/828 |
| 5,114,590 | 5/1992 | Hotier et al. | 219/659 |
| 5,122,275 | 6/1992 | Rasche | 210/659 |
| 5,156,736 | 10/1992 | Schoenrock | 210/264 |

(List continued on next page.)

Primary Examiner—Ernest G. Therkorn
Attorney, Agent, or Firm—Gerald L. Coon

[57] ABSTRACT

This invention relates to a process for separating epsilon caprolactam from a feed mixture comprising epsilon caprolactam and octahydrophenazine which process comprises contacting under adsorption conditions said mixture with an adsorbent, selectively adsorbing said epsilon caprolactam to substantial exclusion of said octahydrophenazine, removing the non-adsorbed portion of the feed mixture from contact with the adsorbent, and thereafter recovering high purity epsilon caprolactam by desorption under desorption conditions. The process can also be conducted in a batch or semi-batch manner or in a continuous manner using moving bed or simulated moving bed technologies.

19 Claims, 5 Drawing Sheets

U.S. PATENT DOCUMENTS

| | | | |
|---|---|---|---|
| 5,159,131 | 10/1992 | Zinnen | 585/828 |
| 5,171,922 | 12/1992 | Anderson | 585/805 |
| 5,227,570 | 7/1993 | Tan | 585/822 |
| 5,238,826 | 8/1993 | Leleu et al. | 435/105 |
| 5,245,029 | 9/1993 | Inaba | 540/540 |
| 5,262,144 | 11/1993 | McCulloch | 423/328.2 |
| 5,264,571 | 11/1993 | Fuchs | 540/540 |
| 5,276,246 | 1/1994 | McCulloch et al. | 585/829 |
| 5,284,992 | 2/1994 | Hotier et al. | 585/805 |
| 5,329,060 | 7/1994 | Swift | 585/805 |
| 5,362,870 | 11/1994 | Higashio | 540/540 |
| 5,370,786 | 12/1994 | Cottrell et al. | 208/62 |
| 5,378,440 | 1/1995 | Herbst et al. | 423/210 |
| 5,382,747 | 1/1995 | Kulprathipanja | 585/828 |
| 5,401,476 | 3/1995 | Hotier et al. | 422/222 |
| 5,405,992 | 4/1995 | Funk et al. | 560/265 |
| 5,440,032 | 8/1995 | Hirosawa | 540/540 |
| 5,453,560 | 9/1995 | Kulprathipanja | 585/828 |
| 5,456,825 | 10/1995 | Negawa et al. | 210/98 |
| 5,457,260 | 10/1995 | Holt | 585/820 |
| 5,459,261 | 10/1995 | Higashio | 540/540 |
| 5,470,482 | 11/1995 | Holt | 210/662 |
| 5,476,985 | 12/1995 | Lansbarkis et al. | 585/825 |
| 5,495,061 | 2/1996 | Kulprathipanja | 585/828 |
| 5,502,248 | 3/1996 | Funk et al. | 562/606 |
| 5,518,625 | 5/1996 | Priegnitz et al. | 210/659 |
| 5,525,725 | 6/1996 | Higashio | 540/540 |
| 5,565,104 | 10/1996 | Priegnitz | 210/659 |
| 5,603,837 | 2/1997 | Ishida et al. | 210/662 |
| 5,618,972 | 4/1997 | Funk et al. | 560/239 |
| 5,629,467 | 5/1997 | Hotier et al. | 585/805 |
| 5,635,072 | 6/1997 | Moran | 210/659 |
| 5,645,729 | 7/1997 | Priegnitz et al. | 210/659 |
| 5,700,358 | 12/1997 | Fuchs | 540/540 |

SEPARATION PROCESSES

BRIEF SUMMARY OF THE INVENTION

1. Technical Field

This invention relates to a process for separating epsilon caprolactam from a feed mixture comprising epsilon caprolactam and octahydrophenazine.

2. Background of the Invention

Epsilon caprolactam is a valuable intermediate which is useful, for example, in the production of nylon 6. Certain processes used to produce epsilon caprolactam generate byproducts, e.g., octahydrophenazine. Conventional separation techniques such as distillation are not effective for separating such mixtures. Accordingly, it would be desirable to separate epsilon caprolactam from its byproducts to give high purity epsilon caprolactam.

3. Disclosure of the Invention

This invention relates to a process for separating epsilon caprolactam from a feed mixture comprising epsilon caprolactam and octahydrophenazine which process comprises contacting under adsorption conditions said mixture with an adsorbent, selectively adsorbing said epsilon caprolactam to substantial exclusion of said octahydrophenazine, removing the non-adsorbed portion of the feed mixture from contact with the adsorbent, and thereafter recovering high purity epsilon caprolactam by desorption under desorption conditions. The process can also be conducted in a batch or semi-batch manner or in a continuous manner using moving bed or simulated moving bed technologies.

DETAILED DESCRIPTION

Figure 1:
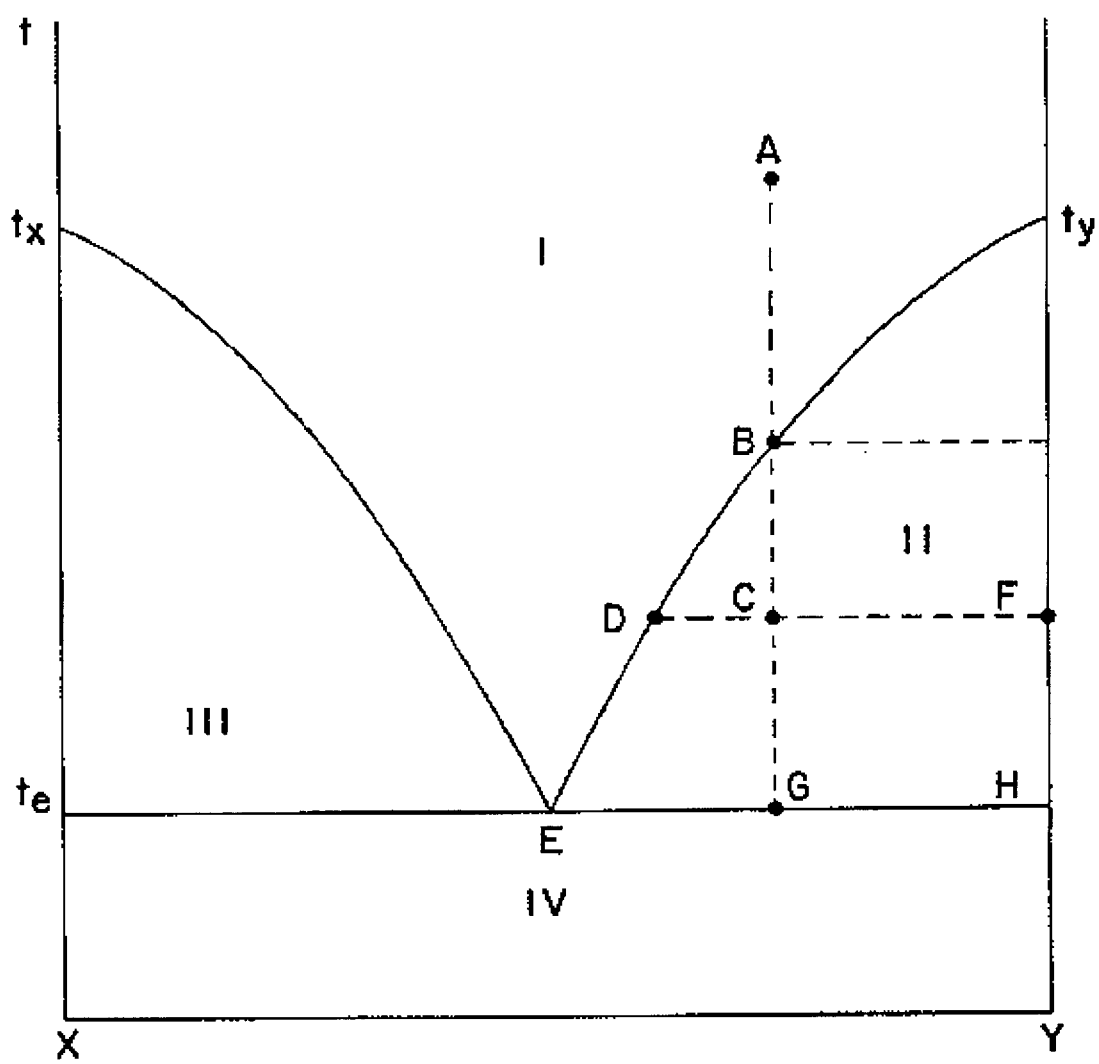
FIG. 1 is a phase diagram illustrating the phenomena involved in the practice of an embodiment of this invention when conglommerates are involved.

In one embodiment, this invention relates to a process for separating epsilon caprolactam from a feed mixture comprising epsilon caprolactam and octahydrophenazine. The process comprises contacting in liquid phase under adsorption conditions, the feed with an adsorbent comprising activated carbon, molecular sieve carbon, molecular sieve or zeolite which selectively adsorbs epsilon caprolactam. The epsilon caprolactam can be recovered by desorption under desorption conditions with a desorbent material comprising a hydrocarbon or water. The individual components of the feed mixture and the desorbent material have boiling points of at least 5° C. difference.

In another embodiment, this invention relates to a process for separating epsilon caprolactam from a feed mixture comprising epsilon caprolactam and octahydrophenazine which process comprises contacting under adsorption conditions said mixture with an adsorbent, selectively adsorbing said octahydrophenazine to substantial exclusion of said epsilon caprolactam, removing the non-absorbed portion of the feed mixture from contact with the adsorbent, and thereafter recovering high purity epsilon caprolactam. The octahydrophenazine can be recovered by desorption under desorption conditions. The process can be conducted in a batch or semi-batch manner or in a continuous manner using moving bed or simulated moving bed technologies.

In yet another embodiment, following the adsorptive separation process, a further step involves crystallizing the epsilon caprolactam from a solution thereof so as to isolate the desired epsilon caprolactam in an even purer form as described hereinbelow. Such coupling technology can provide for a more economical process. Other embodiments of this invention encompass details about feed mixtures, desorbents, flow schemes and operating conditions, all of which are hereinafter disclosed in the following discussion of each of the facets of this invention.

At the outset the definitions of various terms used throughout this specification will be useful in making clear the operation, objects and advantages of the present invention.

A "feed mixture" is a mixture containing one or more extract components and one or more raffinate components to be fed to an adsorbent of the process, i.e., epsilon caprolactam and octahydrophenazine. The term "feed stream" indicates a stream of feed mixture which passes to an adsorbent used in the process.

An "extract component" is a type of compound or a compound that is more selectively adsorbed by the adsorbent while a "raffinate component" is a compound or type of compound that is less selectively adsorbed. In the preferred practice of this process, epsilon caprolactam is the extract component and octahydrophenazine is the raffinate component. The term "raffinate stream" or "raffinate output stream" means a stream through which a raffinate component is removed from an adsorbent. The composition of the raffinate stream can vary from essentially 100% desorbent material (hereinafter defined) to essentially 100% raffinate components. The term "extract stream " or "extract output stream" shall mean a stream through which an extract material which has been desorbed by a desorbent material is removed from the adsorbent. The composition of the extract stream, likewise, can vary from essentially 100% desorbent material to essentially 100% extract components. Although it is possible by the process of this invention to produce high-purity extract product (hereinafter defined) or a raffinate product (hereinafter defined) at high recoveries, it will be appreciated that an extract component is never completely adsorbed by the adsorbent, nor is a raffinate component completely nonadsorbed by the adsorbent. Therefore, small amounts of a raffinate component can appear in the extract stream and likewise, small amounts of an extract component can appear in a raffinate stream.

The extract and raffinate streams then are further distinguished from each other and from the feed mixture by the ratio of the concentrations of an extract component and a specific raffinate component, both appearing in the particular stream. For example, the ratio of concentration of the more selectively adsorbed epsilon caprolactam to the concentration of the less selectively adsorbed octahydrophenazine will be highest in the extract stream, next highest in the feed mixture, and lowest in the raffinate stream. Likewise, the ratio of the less selectively adsorbed octahydrophenazine to the more selectively adsorbed epsilon caprolactam will be highest in the raffinate stream, next highest in the feed mixture, and the lowest in the extract stream.

The term "desorbent material" or "desorbent solvent" shall mean generally a material capable of desorbing an extract component. The term "desorbent stream" or "desorbent input stream" indicates the stream through which desorbent material passes to the adsorbent. When the extract stream and the raffinate stream contain desorbent materials, at least a portion of the extract stream and preferably at least a portion of the raffinate stream from the adsorbent will be passed to separation means, typically fractionators, where at least a portion of desorbent material will be separated at separation conditions to produce an extract product and a raffinate product. The terms "extract product" and "raffinate product" mean products produced by the process containing, respectively, an extract component and a raffinate component in higher concentrations than those in the respective extract stream and the raffinate stream.

The epsilon caprolactam described herein is useful in a variety of applications, such as the manufacture of synthetic fibers (especially nylon 6), plastics, bristles, film, coatings, synthetic leather, plasticizers and paint vehicles, crosslinking agent for polyurethanes, synthesis of amino acid lysine and the like.

Preferred processes include the Beckman rearrangement of cyclohexanone oxime to epsilon caprolactam as disclosed in U.S. Pat. Nos. 3,914,217, 2,221,369, 4,717,770, 5,264,571, 4,804,754, 4,257,950 and 4,789,741, the disclosures of which are incorporated herein by reference. The epsilon caprolactam compositions can be prepared without the need for separating less stable intermediates, and without the need for elaborate separation processes on less stable molecules. This allows for separation at more desirable points in a process for producing epsilon caprolactam thus allowing for improved efficiencies.

Certain conversion processes for epsilon caprolactam yield a product which also contains other closely boiling byproducts or unreacted materials, e.g., octahydrophenazine, cyclohexanone, cyclohexanone oxime, N-cyclohexylidenebutylamine, aniline, isovaleramide, valeramide, isocaproamide, gamma-methyl-gamma-valerolactam, caproamide, adipimide, N-butylacetamide and methylcaprolactam. Therefore the conversion processes ultimately demand the removal of such byproducts or contaminants to yield a high purity epsilon caprolactam product. Isolation and purification of epsilon caprolactam to polymerization grade quality is important due to its principal use in the production of nylon 6 by a polymerization procedure. Thus the presence of impurities pose significant problems due to the sensitivity of such procedures to contamination.

This invention simplifies purification procedures by providing a simple and effective method of removing epsilon caprolactam from octahydrophenazine. Thus it was discovered that certain adsorbents will adsorb epsilon caprolactam to substantial exclusion of octahydrophenazine. Accordingly an appropriate feed mixture for practicing this invention comprises epsilon caprolactam and octahydrophenazine. However, it is impractical to obtain feed mixtures completely free of byproducts, thus suitable feed mixtures can also contain minor portions of other similar boiling point hydrocarbons which may be removed from either the extract or raffinate. Typical sources for the feed mixture of this invention are the processes identified above.

To separate the epsilon caprolactam from a feed mixture in accordance with this invention, the mixture is contacted with the adsorbent and the epsilon caprolactam is more selectively adsorbed and retained by the adsorbent while the other components of the feed mixture are relatively unadsorbed and are removed from the interstitial void spaces between the particles of adsorbent and the surface of the adsorbent. The adsorbent containing the more selectively adsorbed epsilon caprolactam is referred to as a "rich" adsorbent. The epsilon caprolactam is then recovered from the rich adsorbent by contacting the rich adsorbent with a desorbent material.

The term "desorbent material" or "desorbent solvent" as used herein shall mean any fluid substance capable of removing a selectively adsorbed feed component from the adsorbent. Generally, in a swing-bed system in which the selectively adsorbed feed component is removed from the adsorbent by a purge stream, desorbent material selection is not too critical and desorbent materials comprising gaseous hydrocarbons such as methane, ethane, etc., or other types of gases such as nitrogen or hydrogen may be used at elevated temperatures or reduced pressures or both to effectively purge the adsorbed feed component from the adsorbent. However, in adsorptive separation processes which are generally operated continuously at substantially constant pressures and temperatures to ensure liquid phase, the desorbent material relied upon must be judiciously selected to satisfy several criteria.

First, the desorbent material must displace the extract components from the adsorbent with reasonable mass flow rates without itself being so strongly adsorbed as to unduly prevent the extract component from displacing the desorbent material in a following adsorption cycle. Expressed in terms of the selectivity (hereinafter discussed in more detail), it is preferred that the adsorbent be more selective for the extract component with respect to a raffinate component than it is for the desorbent material with respect to a raffinate component. Secondly, desorbent materials must be compatible with the particular adsorbent and the particular feed mixture. More specifically, they must not reduce or destroy the critical selectivity of the adsorbent for the extract components with respect to the raffinate component. Desorbent materials to be used in the process of this invention should additionally be substances which are easily separable from the feed mixture that is passed into the process.

After desorbing the extract components of the feed, both desorbent material and the extract components are typically removed in admixture from the adsorbent. Likewise, one or more raffinate components is typically withdrawn from the adsorbent in admixture with desorbent material and without a method of separating at least a portion of desorbent material, such as distillation, neither the purity of the extract product nor the purity of the raffinate product would be very high. It is therefore contemplated that any desorbent material used in this process will have a substantially different boiling point than that of any individual components of the feed mixture to allow separation of desorbent material from feed components in the extract and raffinate streams by simple fractionation thereby permitting reuse of desorbent material in the process. The term "substantially different" as used herein shall mean that the difference between the boiling points of the desorbent material and the individual components of the feed mixture shall be at least about 5° C. The boiling range of the desorbent material may be higher or lower than that of the feed mixture, preferably lower than that of the feed mixture. In the preferred isothermal, isobaric, liquid-phase operation of the process of this invention, it has been found that the effective desorbent materials comprise hydrocarbons, particularly aliphatic and aromatic hydrocarbons having less than eight carbon atoms, or water.

Illustrative desorbents useful in this invention include, for example, methanol, ethyl ether, cyclopentane, acetone, methyl acetate, isopropyl ether, hexane, methyl cyclopentane, ethyl acetate, ethanol, benzene, cyclohexane, acetonitrile, propanol, propionitrile, water, toluene, cycloheptane, ethylbenzene, p-xylene and cyclooctane.

Certain characteristics of adsorbents are highly desirable, if not absolutely necessary, to the successful operation of a selective adsorption process. Among such characteristics are adsorptive capacity for some volume of an extract component per volume of adsorbent, the selective adsorption of an extract component with respect to a raffinate component and the desorbent material, and sufficiently fast rates of adsorption and desorption of the extract components to and from the adsorbent.

Capacity of the adsorbent for adsorbing a specific volume of one or more extract components is, of course, a necessity; without such capacity the adsorbent is useless for adsorptive separation. Furthermore, the higher the adsorbent's capacity for an extract component the better is the adsorbent. Increased capacity of a particular adsorbent makes it possible to reduce the amount of the adsorbent needed to separate the extract component contained in a particular charge rate of feed mixture. A reduction in the amount of adsorbent required for a specific adsorptive separation reduces the cost of the separation process. It is important that the good initial capacity of the adsorbent be maintained during actual use in the separation process over some economically desirable life.

The second necessary adsorbent characteristic is the ability of the adsorbent to separate components of the feed; or, in other words, that the adsorbent possesses adsorptive selectivity, (B), for one component as compared to another component. Relative selectivity can be expressed not only for one feed component as compared to another but can also be expressed between any feed mixture component and the desorbent material. The selectivity, (B), as used throughout this specification is defined as ratio of the two components of the adsorbed phase over the ratio of the same two components of the unadsorbed phase at equilibrium conditions.

Relative selectivity is shown as Equation 1 below:

$$\text{Selectivity} = (B) = \frac{[\text{vol.percent } C/\text{vol. percent } D]_A}{[\text{vol.percent } C/\text{vol. percent } D]_U} \quad \text{Equation 1}$$

where C and D are two components of the feed represented in volume percent and the subscripts A and U represent the adsorbed and unadsorbed phases respectively. The equilibrium conditions are determined when the feed passing over a bed of adsorbent does not change composition after contacting the bed of adsorbent. In other words, there is no net transfer of material occurring between the unadsorbed and adsorbed phases.

Where selectivity of two components approaches 1.0 there is no preferential adsorption of one component by the adsorbent with respect to the other; they are both adsorbed (or non-adsorbed) to about the same degree with respect to each other. As the (B) becomes less than or greater than 1.0 there is preferential adsorption by the adsorbent for one component with respect to the other.

When comparing the selectivity by the adsorbent of one component C over component D, a (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. While separation of an extract component from a raffinate component is theoretically possible when the selectivity of the adsorbent for the extract component with respect to the raffinate component just exceeds a value of 1.0, it is preferred that such selectivity have a value approaching or exceeding 2. Like relative volatility, the higher the selectivity the easier the separation is to perform. Higher selectivities permit a smaller amount of adsorbent to be used in the process. Ideally desorbent materials should have a selectivity equal to about 1 or less than 1 with respect to all extract components so that all of the extract components can be extracted as a class and all raffinate components clearly rejected into the raffinate stream.

The third important characteristic is the rate of exchange of the extract component of the feed mixture material, or in other words, the relative rate of desorption of the extract component. This characteristic relates directly to the amount of desorbent material that must be employed in the process to recover the extract component from the adsorbent; faster rates of exchange reduce the amount of desorbent material needed to remove the extract component and therefore permit a reduction in the operating cost of the process. With faster rates of exchange, less desorbent material has to be pumped through the process and separated from the extract stream for reuse in the process. The rate of exchange of an extract component with the desorbent is related to the width of the peak envelopes usually measured at half intensity.

A fourth important property of the adsorbent is the absence of reactivity or catalytic function that would cause undesirable chemical changes to the feed and desorbent components. Zeolitic materials are known to react with hydrocarbons, particularly olefins. In contradistinction to such chemically active adsorbents, the carbon adsorbents of this invention are chemically inert to the components of the process streams.

In order to test various adsorbents and desorbent material with a particular feed mixture to measure the adsorbent characteristics of adsorptive capacity and selectivity and exchange rate, a dynamic testing apparatus is employed. The apparatus consists of an adsorbent chamber of approximately 70 cubic centimeter volume having inlet and outlet portions at opposite ends of the chamber. The chamber is contained within a temperature control means and, in addition, pressure control equipment is used to operate the chamber at a constant predetermined pressure. Chromatographic analysis equipment can be attached to the outlet line of the chamber and used to analyze "on-stream" the effluent stream leaving the adsorbent chamber or samples can be removed from the apparatus for chromatographic analysis.

A pulse test, performed using this apparatus and the following general procedure, is used to determine selectivities and other data for various adsorbent systems. The adsorbent is filled to equilibrium with a particular desorbent by passing the desorbent material through the adsorbent chamber. At a convenient time, a pulse feed containing known concentrations of octahydrophenazine and epsilon caprolactam diluted in desorbent is injected. Desorbent flow is resumed and the feed is eluted as in a liquid-solid chromatographic operation. The effluent can be analyzed by on stream chromatographic equipment and traces of the envelopes of corresponding component peaks developed. Alternately, effluent samples can be collected periodically and later analyzed separately by gas chromatography.

From information derived from the chromatographic traces, adsorbent performance can be rated in terms of capacity index for an extract component, selectivity for one component with respect to another, and the rate of desorption of an extract component by the desorbent. The capacity index may be characterized by the distance between the center of the peak envelope of the selectively adsorbed component and some other known reference point. It is expressed in terms of the volume in cubic centimeters of desorbent pumped during this time interval. Selectivity, (B), for an extract component with respect to a raffinate component may be characterized by the ratio of the distance between the center of an extract component peak envelope and the tracer peak envelope (or other reference point) to the corresponding distance between the center of a raffinate component peak envelope and the tracer peak envelope. The rate of exchange of an extract component with the desorbent can generally be characterized by the width of the peak envelopes at half intensity. The narrower the peak width the faster the desorption rate. The desorption rate can also be characterized by the distance between the center of the tracer peak envelope and the disappearance of an extract component which has just been desorbed. This distance is again the volume of desorbent pumped during this time interval.

The adsorbent used in the process of this invention comprises any adsorbent that selectively adsorbs epsilon caprolactam to substantial exclusion of octahydrophenazine. Suitable adsorbents include, for example, activated carbon, molecular sieve carbon, and molecular sieves of the zeolitic variety, i.e., zeolites, and the non-zeolitic variety, i.e., molecular sieves. Illustrative of suitable adsorbents include those permissible adsorbents described in Kirk-Othmer, Encyclopedia of Chemical Technology, Fourth Edition, 1996, the pertinent portions of which are incorporated herein by reference.

Activated carbon is a common, commercially available material, such as Calgon Corporation's "Type F400" granular carbon, "PURASIV", Type PCB as described in Calgon's brochure No. 23-108a, dated August 1978, incorporated herein by reference, is an activated carbon having a large micropore volume, the range of 15 to 20 Angstrom units in diameter, permeated by a system of macropores larger than 1000 Angstroms in diameter. PURASIV is a beaded activated carbon made from molten petroleum pitch shaped into spherical particles and subsequently carbonized and activated.

The term "molecular sieve carbon" as used herein is not intended to necessarily distinguish from those materials referred to as "activated carbon" but to ensure that no material effective for use in the present invention is excluded. There is considerable overlap between the two terms in question and probably in most instances, for purposes of the present invention, the terms are interchangeable. The particular molecular sieve carbons useful in this invention are those having an average pore size greater than about 5 Angstrom units and less than about 12 Angstrom units, preferably between about 5.5 and about 10 Angstrom units, and more preferably between about 5.5 and about 8 Angstrom units.

The adsorbent to be used in the process of this invention may also comprise molecular sieves of the zeolitic variety, i.e., zeolites, and molecular sieves of the non-zeolitic variety, i.e., molecular sieves. Illustrative zeolites useful in this invention include, for example, LZ-10, LZ-20, 4A, 5A, 13X, 10X, Y, SK40, SK41, chabazite, faujasite, levynite, gismondine, erionite, sodalite, analcime, gmelinite, harmotome, mordenite, epistilbite, heulandite, stilbite, edingtonite, mesolite, natrolite, scolecite, thomsonite, brewsterite, laumontite, phillipsite, the ZSM's (ZSM-5, ZSM-20, ZSM-12, and ZSM-34), and the like. Illustrative zeolites useful in this invention are disclosed in U.S. Pat. Nos. 3,702,886, 3,972,983, 3,832,449, 4,086,186 and 3,308,069, the disclosure of which are incorporated herein be reference.

Illustrative molecular sieves useful in this invention include, for example, the silica molecular sieves, such as silicalite (S115) as depicted in U.S. Pat. Nos. 4,061,724 and 4,073,865, the disclosures of which are incorporated herein by reference. Other molecular sieves useful in this invention include crystalline microporous molecular sieve oxides that are based on the presence of aluminophosphate in the framework of the crystal structures, e.g., those commonly known by the acronyms SAPO, MeAPO, FAPO, MAPO, MnAPO, CoAPO, ZAPO, MeAPSO, FAPSO, MAPSO, MNAPSO, CoAPSO, ZAPSO, EIAPO, ELAPSO and the like. Such molecular sieves are described, for example, in U.S. Pat. Nos. 4,567,029, 4,440,871, 4,500,651, 4,554,143 and 4,310,440, the disclosures of which are incorporated herein by reference.

The zeolite and molecular sieve adsorbents preferably have a pore size greater than about 5 Angstrom units and less than about 12 Angstrom units, preferably between about 5.5 and about 10 Angstrom units. Of course the adsorbents may contain meso- and macro-pores along with the preferred pore sizes. It has been discovered by this invention that certain adsorbents will adsorb the epsilon caprolactam to substantial exclusion of octahydrophenazine.

The adsorbent may be in the form of particles such as extrudate, aggregates, tablets, macrospheres or granules having a desired particle range, preferably from about 4 to about 60 mesh (Standard U.S. Mesh). Less water content in the adsorbent is advantageous from the standpoint of less water contamination of the product unless water is the desorbent.

The adsorbent may be employed in the form of a dense fixed bed which is alternatively contacted with a feed mixture and a desorbent material in which case the process will be only semi-continuous. In another embodiment, a set of two or more static beds of adsorbent may be employed with appropriate valving so that a feed mixture can be passed through one or more adsorbent beds of a set while a desorbent material can be passed through one or more of the other beds in a set. The flow of a feed mixture and a desorbent material may be either up or down through an adsorbent in such beds. Any of the conventional apparatus employed in static bed fluid-solid contacting may be used.

Moving bed and simulated moving bed flow systems, however, have a much greater separation efficiency than fixed bed systems and are therefore preferred. In the moving bed or simulated moving bed processes, the retention and displacement operations are continuously taking place which allow both continuous production of an extract and a raffinate stream and the continual use of feed and displacement fluid streams. One preferred embodiment of this process utilizes what is known in the art as the simulated moving bed countercurrent flow system. In such a system, it is the progressive movement of multiple liquid access points down an adsorbent chamber that simulates the upward movement of adsorbent contained in the chamber. Reference can also be made to U.S. Pat. No. 2,985,589, in which the operating principles and sequence of such a flow system are described, and to a paper entitled, "Continuous Adsorptive Processing—A New separation Technique" by D. B. Broughton presented at the 34th Annual Meeting of the Society of Chemical Engineers at Tokyo, Japan on Apr. 2, 1969, both references incorporated herein by reference, for further explanation of the simulated moving bed countercurrent process flow scheme.

Another embodiment of a simulated moving bed flow system suitable for use in the process of the present invention is the co-current high efficiency simulated moving bed process disclosed in U.S. Pat. No. 4,402,832, the disclosure of which is incorporated by reference herein.

It is contemplated that at least a portion of the extract output stream will pass into a separation means wherein at least a portion of the desorbent material can be separated at separating conditions to produce an extract product containing a reduced concentration of desorbent material. Preferably, but not necessary to the operation of the process, at least a portion of the raffinate output stream will also be passed to a separation means wherein at least a portion of the desorbent material can be separated at separating conditions to produce a desorbent stream which can be reused in the process and a raffinate product containing a reduced concentration of desorbent material. In the extract product and the raffinate product, the concentration of desorbent material will be less than about 5 vol. % and more preferably less than about 1 vol. %. The separation means will typically be a fractionation column, the design and operation of which is well known to the separation art.

Although both liquid and vapor phase operations can be used in many adsorptive separation processes, liquid-phase operation is preferred for this process because of the lower temperature, lower energy requirements, smaller equipment size and because of the higher yields of an extract product that can be obtained with liquid-phase operation over those obtained with vapor-phase operation. Adsorption conditions will include a temperature range of from about 20° C. to about 250° C., with about 50° C. to about 200° C. being more preferred, and a pressure sufficient to maintain liquid phase. Desorption conditions will include the same range of temperatures and pressures as used for adsorption conditions.

The size of the units which can utilize the process of this invention can vary anywhere from those of pilot-plant scale (see, for example, U.S. Pat. No. 3,706,812) to those of commercial scale and can range in flow rates from as little as a few cubic centimeters an hour up to many thousand gallons per hour.

In another embodiment, the adsorption separation can be followed by crystallization so as to isolate the desired epsilon caprolactam in an even purer form. Such crystallization can be carried out by conventional methods. For example, the crystallization can involve providing an initial solution containing a non-eutectic mixture of epsilon caprolactam and octahydrophenazine, which mixture has a composition in the compositional region where only epsilon caprolactam crystallizes when its solubility limit in the solution is exceeded, and maintaining the solution at a temperature above the eutectic temperature of the mixture and under conditions such that the solubility limit of epsilon caprolactam is exceeded so as to form crystalline epsilon capirolactam containing relatively less of the octahydrophenazine than was present in the initial solution.

Suitable solutions can be provided by using liquid epsilon caprolactam or by melting solid epsilon caprolactam (when melt crystallization is employed). However, suitable solutions usually consist of the epsilon caprolactam dissolved in an appropriate solvent (e.g., in the solvent in which the adsorption separation was conducted). Any solvent which will dissolve the epsilon caprolactam may be used. Examples of suitable solvents are methanol, ethyl ether, cyclopentane, acetone, methyl acetate, isopropyl ether, hexane, methyl cyclopentane, ethyl acetate, ethanol, benzene, cyclohexane, acetonitrile, propanol, propionitrile, water, toluene, cycloheptane, ethylbenzene, p-xylene, cyclooctane, ketones (e.g., acetone), esters (e.g., ethyl acetate), hydrocarbons (e.g., toluene), nitrohydrocarbons (e.g., nitrobenzene) and ethers [e.g., tetrahydrofuran (THF) and glyme]. A mixture of two or more solvents can be employed to maximize the purity and yield of the desired epsilon caprolactam. The solution used may also contain other materials present in the crude reaction product of the epsilon caprolactam-forming reaction (e.g., catalyst and byproducts). The concentration of the epsilon caprolactam in the solvent solution will be limited by the solubility of epsilon caprolactam in the solvent. Illustrative crystallization techniques useful in this invention include solution and melt crystallization such as disclosed in U.S. Pat. Nos. 5,430,194 and 5,675,022, the disclosures of which are incorporated herein by reference.

In the process of this invention the solution containing the epsilon caprolactam is maintained under conditions such that the solubility limit of the desired epsilon caprolactam is exceeded. Such conditions include addition of a non-solvent to the solution, removal of any solvent from the solution and, preferably, cooling the solution (including vacuum cooling the solution). Combinations of these conditions can be used to effect the desired crystallization.

With respect to crystallization by using solvent removal, it should be noted that, if the pressure above the solution is fixed, then adding heat will increase solution temperature until the solution boils. Upon continued addition of heat, solvent will evaporate and the solution will become saturated. At this point, the solution concentration will remain constant (Gibbs Phase Rule) and continued heating will precipitate (crystallize) solute (i.e., the desired epsilon caprolactam). Conversely, if the pressure above the saturated solution which exhibits an increase in solubility with increased temperature is slowly reduced, the temperature of the solution will decrease and cooling will cause precipitation (crystallization) of solute (i.e., the desired epsilon caprolactam).

With respect to crystallization by using non-solvent (e.g., hexane) addition, it should be noted that adding a liquid to the saturated solution that is miscible with the solvent but in which the solute has limited solubility will cause the solute (i.e., the desired epsilon caprolactam) to precipitate (crystallize).

Although the description of this invention appearing below relates primarily to crystallization by cooling, this invention encompasses any conditions for effecting the desired crystallization.

This invention is applicable to the separation of epsilon caprolactam from a mixture containing epsilon caprolactam and the octahydrophenazine, provided the mixture is in the compositional region where only epsilon caprolactam crystallizes on cooling of solution of the mixture. Suitable mixtures include mixtures of conglomerate epsilon caprolactam compounds (illustrated by FIG. 1 which is discussed below).

When epsilon caprolactam being separated is a conglomerate, the crystallization phenomenon that occurs in the practice of this invention is generally governed by the factors illustrated in FIG. 1 which is a phase diagram of two substances, X (i.e., octahydrophenazine) and Y (i.e., epsilon caprolactam). In FIG. 1, area (i.e., compositional region) I represents an unsaturated solution containing X and Y, area (i.e., compositional region) II corresponds to the coexistence of crystals of substance Y and the saturated solution containing X and Y, area (i.e., compositional region) III represents the coexistence of crystals of substance X and the saturated solution containing X and Y, and area (i.e., compositional region) IV corresponds to mixtures of crystals of substances X and Y. The curve separating areas (i.e., compositional regions) I and II is the solubility curve for substance Y, while the curve separating areas (i.e., compositional regions) I and III is the curve for phase equilibrium between solid X and the corresponding solution containing X and Y. The curves intersect at point E, where solid X, solid Y and a solution with composition E, that is saturated with both X and Y are in equilibrium. Points $t_x$ and $t_y$ are the melting points of pure components X and Y, respectively.

If an unsaturated solution containing X and Y (represented by point A in FIG. 1) is cooled, the composition of the solution does not change and the point representing the cooling solution therefore moves vertically downward on the phase diagram (FIG. 1). With continued cooling, this vertical line intersects the solubility curve at point B, lying on the boundary of the region corresponding to the separation of crystals of substance Y. On still further cooling, crystals of only substance Y separate, the solution is depleted in component Y and hence the composition of the solution moves along the solubility curve from right to left. For example, on cooling the solution down to a temperature corresponding to point C, crystals of composition F and the mother liquor (melt or solution) with a composition corresponding to point D are in equilibrium in the weight ratio $\overline{CD}:\overline{CF}$. On a further decrease in temperature, the point representing the liquid phase (solution) moves along the solubility curve towards point E. Finally, at a temperature corresponding to point G, crystals of H are in equilibrium with a solution of composition E. Solution E is saturated with both components, so that the crystals of both components will separate from a liquid phase (solution) with a constant composition at constant temperature $t_e$ on further removal of heat. Temperature $t_e$ is thus the lowest temperature at which crystals of a single component can still be obtained from the solution. For initial solution A, the weight ratio of the maximum obtainable amount of crystals of Y to mother liquor E is given by the ratio of segments $\overline{EG}:\overline{GH}$. Point E is called the eutectic point, temperature $t_E$ is the eutectic temperature and the mixture of substances X and Y with composition corresponding to point E is a eutectic mixture.

The crystallization is conducted using solutions containing non-eutectic epsilon caprolactam mixtures in the compositional region where only the desired epsilon caprolactam is obtained by crystallization. During crystallization by cooling, the relative concentration of the epsilon caprolactam, the uniformity of solution temperature, the cooling rate and the cooling temperature are controlled so that the concentration of the epsilon caprolactam remains in the region where only the desired epsilon caprolactam crystallizes. Thus, with reference to FIG. 1, in order to crystallize only component Y, the relative concentration of epsilon caprolactam must be controlled to be to the right of eutectic concentration (E). During the crystallization (when the concentration of Y in the solution shifts to the left on the solubility curve toward the eutectic concentration, E), the appropriate concentration is maintained by stopping crystallization before the eutectic concentration and/or temperature are reached.

The epsilon caprolactam mixtures useful in the process of this invention can have any composition other than the composition at which the mixture is eutectic (i.e., the mixtures are non-eutectic), provided the composition is in the region where only the desired epsilon caprolactam crystallizes on cooling the mixture. The reason for the requirement of using non-eutectic mixtures is that unacceptably large amounts of the undesired byproducts usually crystallize from eutectic mixtures.

In an embodiment of this invention, solutions containing the epsilon caprolactam are cooled to effect crystallization of the desired epsilon caprolactam. The temperature of the solution can be raised slightly after the crystals initially form to a temperature just below the initial crystallization temperature and then the temperature can be lowered again. This technique causes the smaller crystals to redissolve and the larger crystals to grow still larger with the result that better generation of the crystals from the solution is achieved. Crystallization temperature will effect both product purity and yield in that lower temperatures produce higher yields. Vacuum cooling can be used in the practice of this invention.

In another embodiment of this invention, the crystallization can, if desired, be conducted by cooling in stages. That is, the initial solution of the epsilon caprolactam can be cooled to a temperature at which the desired epsilon caprolactam crystallizes and held at that temperature until crystallization is complete. Then the crystals can be filtered from the remaining solution to produce a filtrate and the filtrate can be again cooled to crystallize additional amounts of the desired epsilon caprolactam. The cooling-crystallization-filtration-cooling sequence can be repeated as often as desired. The advantage of operating in stages is increased yield of the desired epsilon caprolactam. It is desirable to remove some of the solvent between each cooling stage.

In the practice of this invention, the crystallization of the desired epsilon caprolactam can be achieved using any convenient apparatus. A preferred apparatus is a falling film crystallizer such as is disclosed in U.S. Pat. No. 3,621,664 and that apparatus contains vertical (usually metallic) wall surfaces which are cooled from the opposite wall surface. When the liquid phase (i.e., the solution of the epsilon caprolactam) flows as a much smaller stream-like film that is spread over the area of the wall, the separation is superior to that obtained when the liquid phase fills the entire cross section of the means, such as a pipe, down which it flows, the wetted circumference and the quantity of flow for the one case being equal to those of the other. The reason for this is that in the case of the film the flow is turbulent, whereas in the other case, for a given example, the flow has a Reynolds Number of 1600, indicating a laminar flow. The turbulent flow in the falling film has a laminar boundary layer a few tenths of a millimeter thick where mass transfer occurs by molecular diffusion, whereas this boundary layer for a completely laminar flow is approximately ten millimeters thick. The equation for the actual distribution coefficient, reproduced in U.S. Pat. No. 3,621,664, shows that a distribution coefficient approaching the best possible value is obtainable with film flow, when the crystallization rate is on the order of one centimeter per hour, as would be required in a large scale operations and, when the molecular diffusion coefficient in the liquid phase is on the order of $10^{-5}$ centimeters$^2$/second; whereas in the other case the distribution coefficient is close to one, indicating virtually no separation. If good separation is wanted in the other case, the Reynolds Number must be raised, which necessitates a larger flow and greater power consumption, particularly with viscous liquids, rendering operation uneconomical.

Good separation of the desired epsilon caprolactam during crystallization can occur in the apparatus of U.S. Pat. No. 3,621,664 even in the laminar region, provided that the waves appearing on the film surface cause a mixing action. Here also the layer thickness is only a few tenths of a millimeter and separation is correspondingly good. The quantity of liquid processed and the power consumed by the circulation pump are relatively little. The cooled vertical walls of the crystallizer are, in a preferred embodiment, in the form of tube bundles having any desired number of vertical, parallel tubes, the liquid being introduced at the tops of the tubes by a distributor to flow down the tubes inner surfaces as a film, and the cooling medium filling the jacket surrounding the tubes. The lower end of the crystallizer incorporates a tank for collecting the liquid phase.

The desired epsilon caprolactam crystals usually form on the inner surface of the falling film crystallizer. The crystals are removed by dissolving the crystals in a solvent (e.g., acetone) at a temperature below the melting point of the desired crystals to avoid substantial degradation of the desired crystals.

Two other arrangements of the apparatus of U.S. Pat. No. 3,621,664 can be used for crystallization in accordance with this invention on an industrial scale. In one arrangement, crystallization occurs on the outer surfaces of a heat exchanger composed of a bundle of thin, parallel tubes, with baffle plates causing a strong cross flow of the liquid phase. In the other arrangement, the crystals form on the outer surface of a horizontal pipe grid, the liquid phase flowing down over the grid. In both arrangements, the cross flow about the pipes causes a turbulence producing a general mixing action, the laminar boundary layer at each pipe being then very thin. Similar results are obtained with cooled or, for some applications, heated short fins or baffle plates positioned in the flow to give a pronounced cross flow.

The separation in the preferred crystallization apparatus may be improved during crystallization by periodically briefly heating (or cooling, in certain applications) the fluid phase before it enters the crystallizer. This measure yields a smooth crystal surface and avoids dendritic or uneven crystal growth with the attendant undesirable trapping of mother liquid within the crystal layer.

Crystallization in the above-mentioned preferred crystallization apparatus is conveniently carried out in a single apparatus in such a manner that single crystallizations are cyclically repeated, beginning with the step of the highest concentration of impurity or impurities and advancing to the step of the desired component in its purest form. The small amount of mother liquor (i.e., solution of the epsilon caprolactam) held on the surfaces of the crystallizer only slightly contaminates the crystallization of the succeeding step and going from the "purest" step to the "least pure" step, when ending one cycle and starting another, does not influence the separation.

The crystallization process can be conducted in the preferred crystallization apparatus in an inert atmosphere. The crystals of the final step can be further purified by distillation or partial melting and the less pure separated substance returned to the final step. The surface on which crystallization occurs can be cooled by flowing a heat exchange medium, in the form of a film, over the opposite surface of the crystallizer wall. This surface can be vertical, horizontal, or at any angle there between.

The crystals of the desired epsilon caprolactam produced by the process of this invention contain considerably less of the other impurities than is contained the starting liquid epsilon caprolactam. However, some of the other impurities may be present in the crystals due to occlusion, incomplete draining or entrainment of the solution from which the crystals are formed. Thus, the process of this invention provides epsilon caprolactam having very high purity. Purities preferably greater than 98%, and more preferably greater than 99%, can be obtained by the process of this invention.

With respect to the embodiment that couples adsorption separation with crystallization, the primary benefit of this technology is that adsorption works best when the purity of the feed stream is from about 10 to about 95% epsilon caprolactam and it is desired to achieve about 95 to 99.5% purity. Crystallization works best when the feed is as pure as possible and it is desired to achieve purities greater than about 99.5%. Another benefit of the coupling technology is that it allows for purification of epsilon caprolactam from solutions where the concentration of epsilon caprolactam is less than or equal to that of the eutectic composition. Hence, with the coupling technology, one can use both adsorption and crystallization in their optimum range allowing for a more economical process. Furthermore, in a standard crystallization process, the mother liquor is either disposed or reworked to improve the yields. With the coupling technology, the mother liquor can be recycled back to the adsorption process for reuse. The coupling technology also allows for less solvent being employed, smaller adsorption columns and, as indicated above, higher purities. Additionally, the coupling of adsorption separation with crystallization may be conducted with the raffinate or the extract. For purifying the raffinate, an advantage exists over purifying the extract because the amount of solvent in the raffinate is typically less than the extract.

Hence, solvent recovery costs are decreased and crystallization costs may be decreased.

For a retentive or extractive process, i.e., the desired species are strongly adsorbed compared to the non-desired species, the coupling technology can be practiced with either solution crystallization or melt crystallization. The advantage of melt crystallization is that one less distillation column is used. Of course, some chemical species crystallize from solution a lot easier than from the melt.

Figure 2:
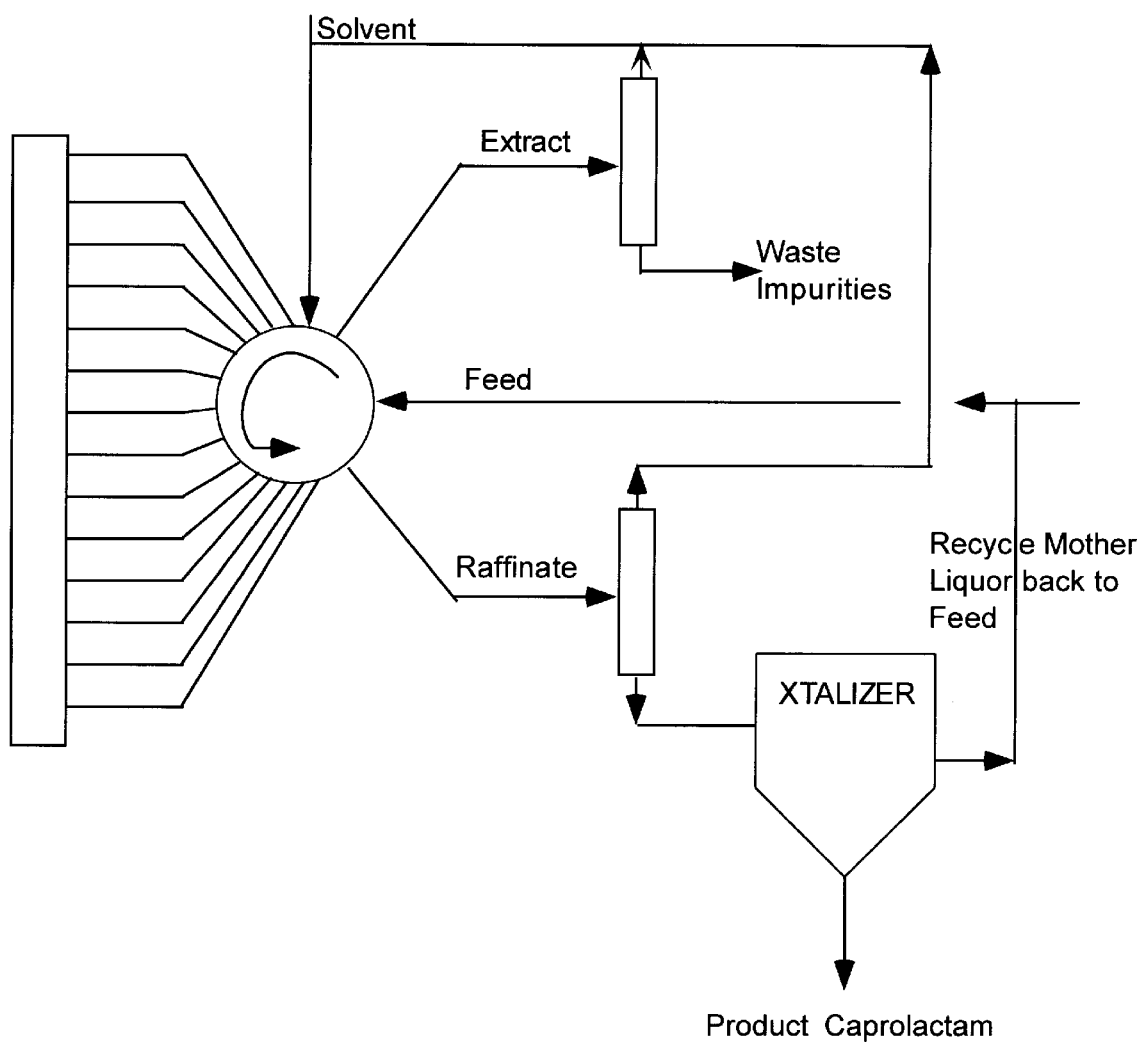
FIG. 2 depicts a reaction flow scheme where the desired species is non-retentive and melt crystallization is used.

As indicated above, FIG. 2 depicts an example where the desired species is non-retentive and melt crystallization is used. The feed is fed to the simulated moving bed process to which a desorptive solvent is also fed. The extract, containing the undesired species is sent to a distillation column (or more preferably a flash tank if the solvent is volatile enough) to recover the solvent. This solvent is recycled to the solvent feed stream. The raffinate, containing the desired species, is sent to a distillation column wherein the solvent is recovered and recycled back to the solvent feed system. The bottoms from the column (in a heated state to keep the material fluid) are sent to a crystallizer where the desired product is further refined from the melt. The crystals are removed as the product and the mother liquor is recycled back to the feed to the simulated moving bed.

Figure 3:
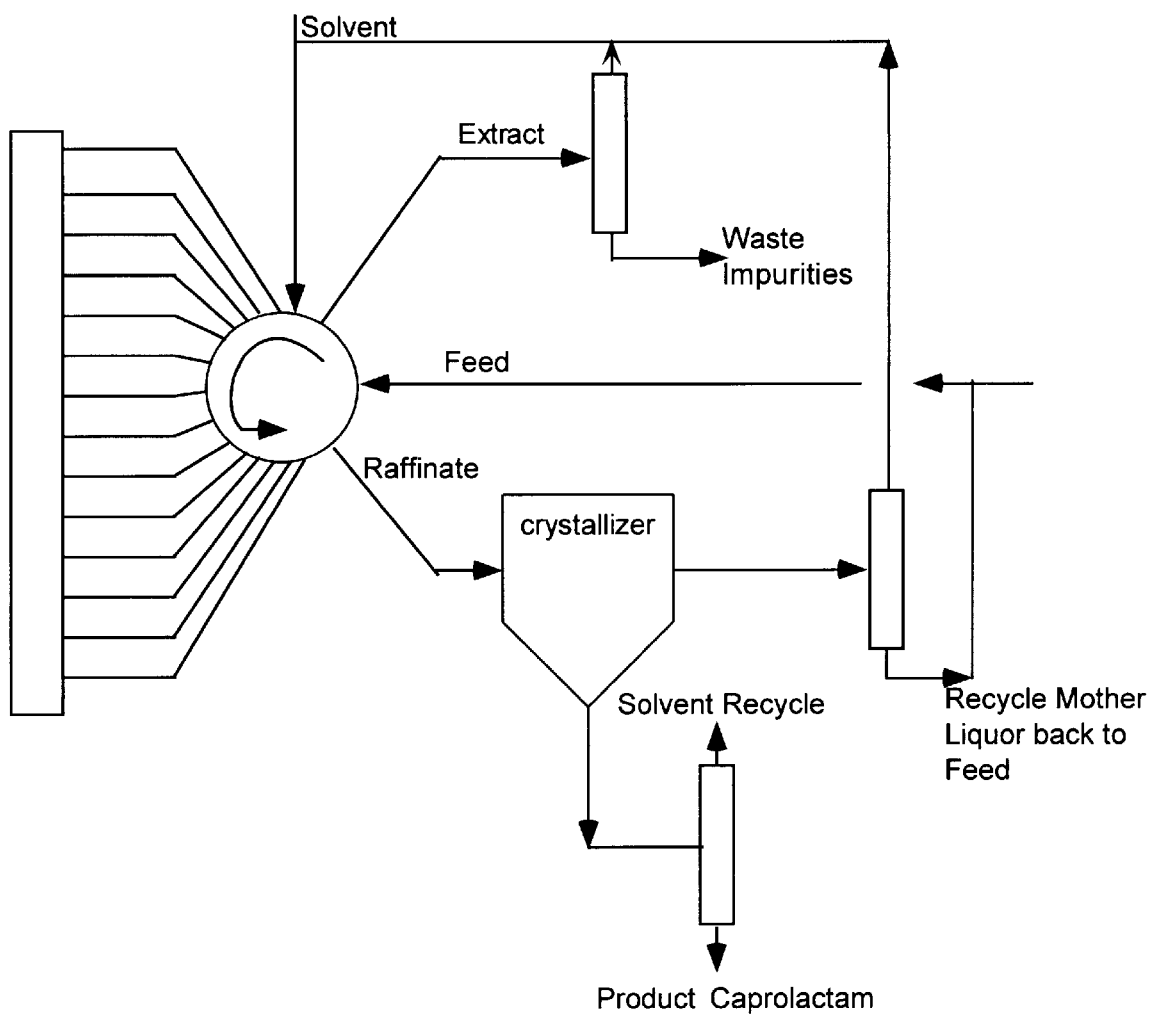
FIG. 3 depicts a reaction flow scheme where the desired species is non-retentive and solution crystallization is used. In comparison with FIG. 2, another solvent reclamation column is added.
Figure 4:
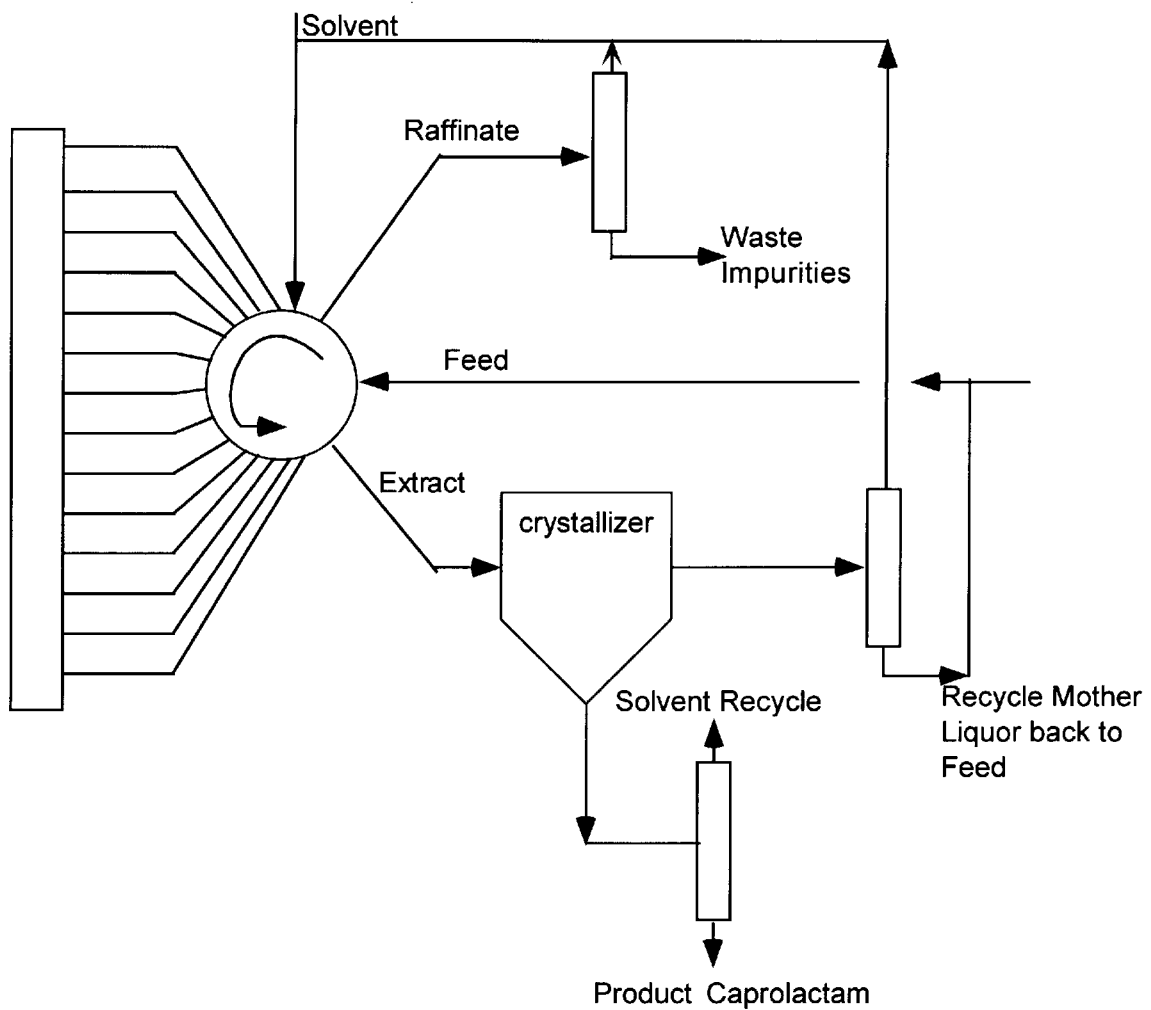
FIG. 4 depicts a reaction flow scheme where the extract contains the desired species and solution crystallization is used. In comparison with FIG. 3, the raffinate and extract streams are switched.
Figure 5:
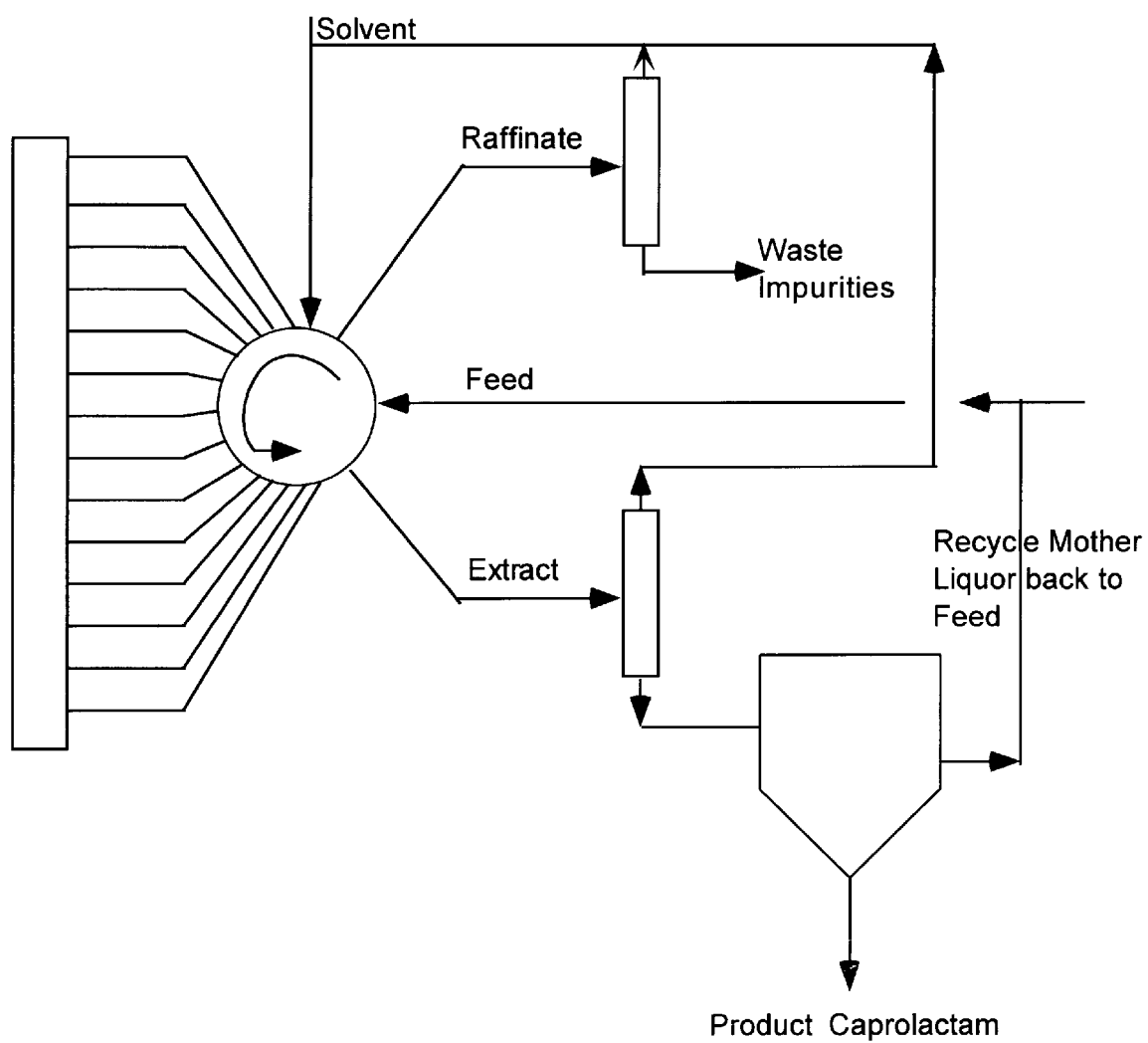
FIG. 5 depicts a reaction flow scheme where the extract contains the desired species and melt crystallization is used.

As indicated above, FIG. 3 depicts an example when melt crystallization cannot be used and solution crystallization can be. The flow diagram changes somewhat and another solvent reclamation column is added. The process is basically the same as depicted in FIG. 2 except the raffinate, again containing the desired species, is first sent to a crystallizer where the product is crystallized. Of course, an added column can be placed to adjust the amount of solvent in the stream being fed to the crystallizer. The product is then dried in a distillation column (or other dryer) whilst the mother liquor is sent to a distillation column wherein the solvent is recovered and the bottoms from the solvent recovery column are sent back to the feed to the simulated moving bed.

I claim:

1. A process for separating epsilon caprolactam from a feed mixture comprising epsilon caprolactam and octahydrophenazine which process comprises contacting under adsorption conditions said mixture with an adsorbent, selectively adsorbing said epsilon caprolactam to substantial exclusion of said octahydrophenazine, removing the non-adsorbed portion of the feed mixture from contact with the adsorbent, and thereafter recovering high purity epsilon caprolactam by desorption under desorption conditions.

2. The process of claim 1 wherein the adsorbent is selected from an activated carbon, molecular sieve carbon, molecular sieve and zeolite.

3. The process of claim 2 wherein the molecular sieve carbon, molecular sieve and zeolite have a pore size greater than about 5 Angstrom units and less than about 12 Angstrom units.

4. The process of claim 1 wherein the adsorbent is silicalite or a Y zeolite.

5. The process of claim 1 wherein said adsorption and desorption conditions include a temperature of from about 20° C. to about 250° C. and a pressure sufficient to maintain a liquid phase.

6. The process of claim 1 wherein the desorbent material comprises an olefinic hydrocarbon having eight or less carbon atoms or mixtures thereof or water.

7. The process of claim 6 wherein the desorbent material is methanol or acetonitrile.

8. The process of claim 1 wherein said separation is effected by means of a simulated moving bed flow scheme.

9. The process of claim 8 wherein said simulated moving bed scheme uses a countercurrent flow.

10. The process of claim 8 wherein said simulated moving bed scheme uses a co-current flow.

11. The process of claim 1 further comprising subjecting said high purity epsilon caprolactam to crystallization.

12. The process of claim 11 wherein said crystallization comprises solution or melt crystallization.

13. The process of claim 11 wherein mother liquor from said crystallization is recycled back to the adsorption separation.

14. The process of claim 11 wherein said crystallization comprises providing an initial solution containing a non-eutectic mixture of epsilon caprolactam and octahydrophenazine, which mixture has a composition in the compositional region where only epsilon caprolactam crystallizes when its solubility limit in the solution is exceeded, and maintaining the solution at a temperature above the eutectic temperature of the mixture and under conditions such that the solubility limit of epsilon caprolactam is exceeded so as to form crystalline epsilon caprolactam containing relatively less of the octahydrophenazine than was present in the initial solution.

15. The process of claim 14 which involves cooling the initial solution in a falling film crystallizer to achieve crystallization of epsilon caprolactam on a surface of the crystallizer.

16. A process for separating epsilon caprolactam from a feed mixture comprising epsilon caprolactam and octahydrophenazine which process comprises contacting under adsorption conditions said mixture with an adsorbent, selectively adsorbing said octahydrophenazine to substantial exclusion of said epsilon caprolactam, removing the non-adsorbed portion of the feed mixture from contact with the adsorbent, and thereafter recovering high purity epsilon caprolactam.

17. The process of claim 16 further comprising subjecting said high purity epsilon caprolactam to crystallization.

18. The process of claim 17 wherein said crystallization comprises solution or melt crystallization.

19. The process of claim 17 wherein mother liquor from said crystallization is recycled back to the adsorption separation.

* * * * *